(12) United States Patent
Le Comte et al.

(10) Patent No.: US 6,333,197 B1
(45) Date of Patent: Dec. 25, 2001

(54) METHOD AND DEVICE FOR FRACTIONATED DISTRIBUTION OF A BLOOD SAMPLE

(75) Inventors: Roger Le Comte, Perols; Henri Champseix, Montferrier sur Lez, both of (FR)

(73) Assignee: A B X, Montpellier Cedex (FR)

( * ) Notice: Subject to any disclaimer, the term of this patent is extended or adjusted under 35 U.S.C. 154(b) by 0 days.

(21) Appl. No.: 09/170,112

(22) Filed: Oct. 13, 1998

(30) Foreign Application Priority Data

Oct. 28, 1997 (FR) .................................................. 97 13503

(51) Int. Cl.[7] .............................. G01N 35/08; G01N 1/10
(52) U.S. Cl. .................................. 436/52; 436/47; 436/53; 436/179; 422/67
(58) Field of Search ............................. 436/179, 47, 52, 436/53; 422/67

(56) References Cited

U.S. PATENT DOCUMENTS

| | | | |
|---|---|---|---|
| 3,804,593 | 4/1974 | Smythe et al. | 436/53 |
| 4,022,575 * | 5/1977 | Hansen et al. | 436/52 |
| 4,177,677 * | 12/1979 | Ruzicka et al. | 73/422 |
| 4,207,074 * | 6/1980 | Suzuki | 73/864.12 |
| 4,224,033 * | 9/1980 | Hansen et al. | 436/53 |
| 4,272,483 * | 6/1981 | Schick | 422/67 |
| 4,645,647 * | 2/1987 | Yoshida et al. | 422/81 |
| 4,853,336 * | 8/1989 | Saros et al. | 436/53 |
| 4,865,811 | 9/1989 | Newton et al. | 422/81 |
| 4,952,372 * | 8/1990 | Huber | 422/81 |
| 5,221,521 * | 6/1993 | Hashizume et al. | 422/100 |
| 5,569,861 | 10/1996 | Le Comte et al. | 73/864.22 |
| 5,695,720 * | 12/1997 | Wade et al. | 422/82 |
| 5,741,709 * | 4/1998 | Hsu | 436/52 |

FOREIGN PATENT DOCUMENTS

| | | |
|---|---|---|
| 853704 | 10/1977 | (BE) . |
| 2192708 | 2/1974 | (FR) . |
| 07318566 | 12/1995 | (JP) . |

* cited by examiner

Primary Examiner—Maureen M. Wallenhorst
Assistant Examiner—Latoya I. Cross
(74) Attorney, Agent, or Firm—Dennison, Scheiner, Schultz & Wakeman

(57) ABSTRACT

A method for fractionated distribution of a blood sample, includes the steps of:

a) drawing up a blood sample into a needle;

b) distributing via the needle an aliquot corresponding to a specific fraction of the blood sample drawn up, into a flow of a reagent, to thereby produce a mixture of the aliquot and of the reagent;

c) collecting the mixture in a mixing and/or measuring receptacle; and d) repeating steps b) and c) at least once to distribute a further aliquot corresponding to a further specific fraction of the blood sample, into a further flow of reagent.

9 Claims, 3 Drawing Sheets

METHOD AND DEVICE FOR FRACTIONATED DISTRIBUTION OF A BLOOD SAMPLE

BACKGROUND OF THE INVENTION

The invention relates to the field of haematological analysis, and more specifically to the fractionated distribution of a blood sample.

The expression "blood sample" in this case denotes a volume of blood obtained from a blood sample taken from a patient, and contained in an analysis container, which for example can be an open tube, or a tube closed by a stopper. In general the blood in question is whole or full blood, taken with an anticoagulant.

In haematological analysis, it is often necessary to obtain several fractions of the blood of a patient, which are still known as "aliquots", and are destined to be diluted with different reagents in order to obtain different analysis results.

This is the case in particular for globule counters, which count and differentiate white globules.

For practical reasons, it is preferable to take only a single sample of the patient's blood in a tube, then to fractionate this sample into different aliquots, each of which will then be added to a suitable reagent.

For this purpose, fractionating of the blood sample by means of a sample valve is known, according to the teaching, for example, of publication FR 2 622 692 in the name of the applicant.

These sampling valves have the advantage that they operate at high speeds, which makes them particularly advantageous for specific types of analysers.

However, their main disadvantages are that they require volumes of blood which are far greater than the theoretical volumes necessary for the analysis, they have a complex and costly structure, and they additionally need frequent cleaning, which is difficult to carry out.

In the field of biochemistry, it is also known to collect all of a blood serum in a needle, and then to discharge various successive volumes of this sample, for the purpose of different dilutions.

This specific technique is used for a blood serum, in other words blood from which the globules have been removed, and which thus has lower viscosity than whole or full blood.

SUMMARY OF THE INVENTION

The object of the invention is in particular to eliminate the aforementioned disadvantages, and to permit fractionated distribution of a blood sample, in highly efficient conditions.

In particular, an object of the invention is to provide fractionated distribution, using means which are simple, reliable, and easy to maintain.

A further object of the invention is to permit distribution of this type on the basis of a minimal blood sample volume, without any risk of contamination of the reagents with one another, and in each case ensuring that an aliquot of blood is well mixed with the reagent concerned.

For this purpose, the invention provides a method for fractionated distribution of a blood sample, comprising the following operations:

a) drawing up a blood sample into a needle;
b) distributing via the needle an aliquot of blood, corresponding to a specific fraction of the sample drawn up, into a flow of a reagent, in order to produce a mixture of the aliquot and the reagent;
c) collecting the mixture in a mixing and/or measuring receptacle; and
d) repeating operations b) and c) at least once on another aliquot of the same sample, and another flow of reagent.

Thus, the method according to the invention makes it possible to fractionate a blood sample contained in a needle, into at least two aliquots which are each mixed by dilution with an appropriate reagent, in each case in a mixing and/or measuring receptacle.

As a result, each aliquot, which corresponds to a specific fraction of the sample, is forced into the flow of reagent, thus permitting thorough mixing of the blood and reagent to be analysed.

The aliquots have selected volumes which can be identical or different, thus providing the method according to the invention with considerable flexibility of use.

The above-described operation a) advantageously comprises drawing up the blood sample into the needle which already contains a fluid, a bubble of gas, for example of air, being formed on the interface between the fluid and the blood sample.

By this means, there is no risk of mixing taking place between the blood sample and the fluid, since the latter simply acts as an intermediary for drawing up the sample, and then for gradual ejection of this sample in various aliquots, according to the analyses to be carried out.

According to another characteristic of the invention, the blood sample is drawn up into the needle from a tube of an open or closed type, containing a volume of blood to be analysed.

The blood sample which is drawn up into the needle advantageously has a volume which is greater than the sum of the respective volumes of the aliquots to be distributed, such as to provide an optional excess of volume, in order to obtain an initial volume of blood in the needle on completion of the operation a), and/or a residual volume of blood in the needle on completion of the operation d), thus making it possible to keep the aliquots intact.

The initial volume of blood can be discharged before the fractionated distribution takes place.

The residual volume of blood alone is affected if there is residual fluid present before sampling of the blood takes place. This residual volume can be discharged after the distribution, for example into a rinsing vessel, which allows the needle to be used to collect a further blood sample.

According to a further characteristic of the invention, the operation b) comprises injection of the aliquot of blood and injection of the flow of reagent under controlled conditions, and substantially simultaneously.

According to a preferred embodiment of the invention, this operation b) comprises in succession:

b1) injection of an initial part only of the flow of reagent;
b2) simultaneous injection of the aliquot of blood and of an intermediate part of the flow of reagent; and
b3) injection of a final part only of the flow of reagent.

According to a further characteristic of the invention, in operation b), the flow of reagent is injected such that this flow reaches the end of the needle by means of which the aliquot of blood is injected.

The aliquot of blood is preferably injected in a substantially vertical descending direction, whereas the flow of reagent is injected in a direction which is horizontal or inclined relative to the horizontal, such as to assist rotary motion or eddying, thus permitting thorough mixing of the blood and the reagent.

The method according to the invention can comprise at least one additional operation, consisting of depositing an aliquot of blood in a fluid medium or on a solid support, for example on a glass plate.

This makes it possible to combine operations of mixing aliquots and reagents, with operations of a different kind.

According to another aspect, the invention relates to a device for implementation of the above-described method, comprising:

a needle which can draw up a blood sample;

a first volumetric distributor, which is connected to the needle, in order to draw up and eject selected volumes of blood;

at least one reagent injection nozzle, which can be disposed in the vicinity of the end of the needle;

a second volumetric distributor, which is connected to the nozzle, in order to eject selected volumes of a flow of reagent;

a control unit which is connected to the first volumetric distributor and to the second volumetric distributor (s), in order to actuate the latter in a coordinated manner; and at least one mixing and/or measuring receptacle, in order to collect the mixture formed from the blood and the reagent, which are distributed respectively by the needle and the injection nozzle.

The injection nozzle is preferably oriented towards the open end of the needle, via which the blood is ejected.

The needle is advantageously substantially vertical, with its open end facing downwards, whereas the injection nozzle extends in a direction which is horizontal or inclined relative to the horizontal.

The injection nozzle is advantageously integral with a mixing and/or measuring receptacle.

This receptacle can be a vessel which is delimited by a peripheral wall, the injection nozzle opening into the vessel in the vicinity of the peripheral wall.

According to a variant embodiment, the receptacle is a T-shaped connection with a first, a second and a third branch, wherein the free end of the needle opens into the first branch, the second branch acts as an injection nozzle for the reagent, and the third branch constitutes an outlet for the mixture.

According to a preferred embodiment of the invention, the device comprises motor means, which can displace the needle, and bring it in succession towards the receptacles, under the control of the control unit.

It will be appreciated that the needle can be fixed, and the receptacles can be brought in succession close to the needle.

The first volumetric distributor and the second volumetric distributor(s) each advantageously comprise at least one syringe piloted by a motor, which is for example of the step type.

The following description, which is provided by way of example, refers to the attached drawings.

DESCRIPTION OF THE PREFERRED EMBODIMENTS

Figure 1:
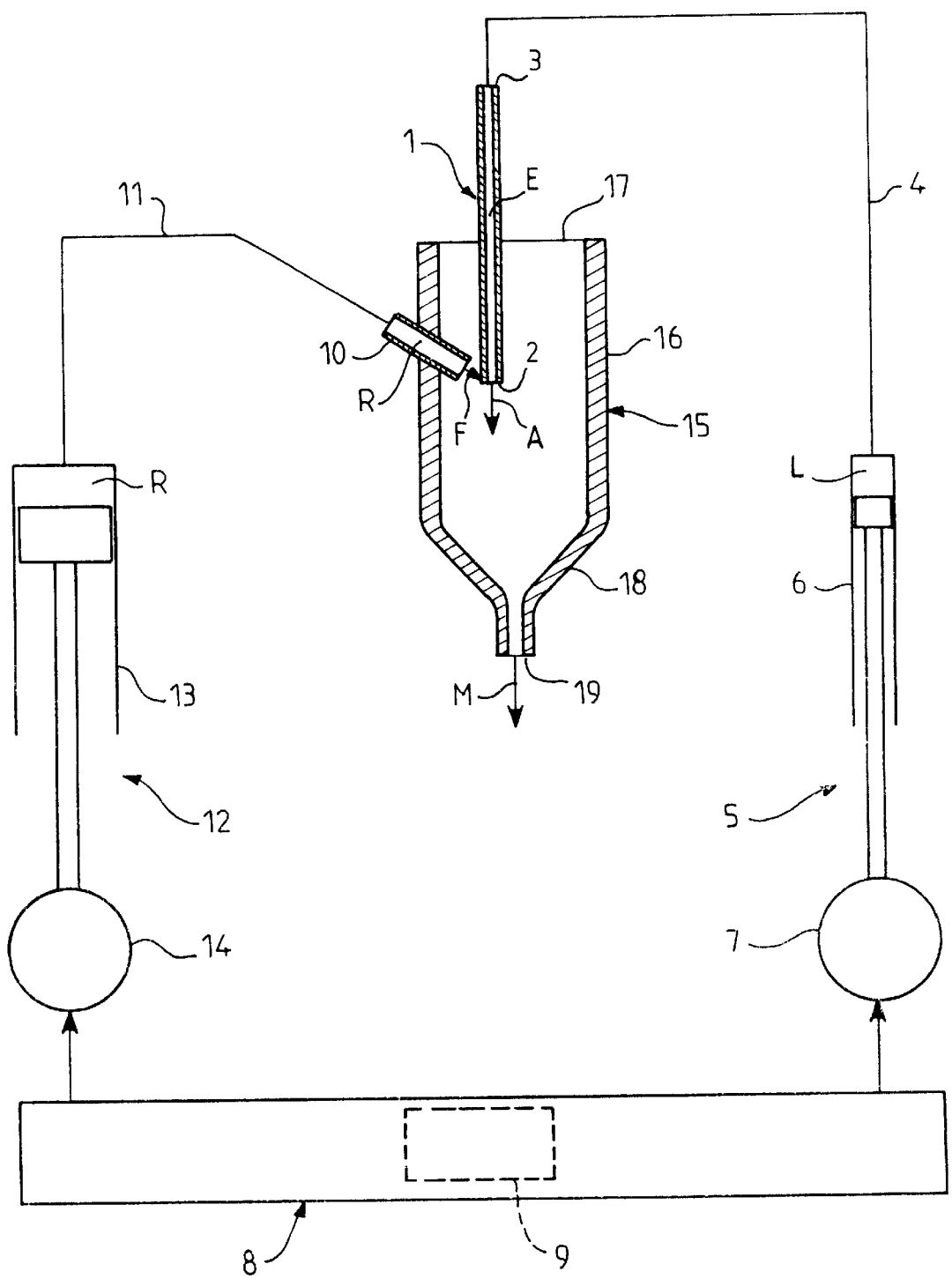
FIG. 1 shows schematically a distribution device according to the invention, of which, for the sake of simplification, a single mixing and/or measuring vessel is shown.

The device in FIG. 1 comprises a needle 1, which can contain a blood sample E, this needle extending in a substantially vertical direction and having a lower end 2 which is open, and an upper end 3 which is connected by means of a duct 4 to a first volumetric distributor 5, consisting of a syringe 6 actuated by a step motor 7. A control unit 8 comprising a microprocessor 9 is provided in order to pilot the step motor 7, and thus allow the needle to draw up the blood sample E, and then to eject the fractions or aliquots of this sample under controlled conditions, as will be described hereinafter.

A fluid L which fills the syringe 6, the duct 4 and partially the needle 1, acts as an intermediary in order to control the steps of drawing up into, and ejection from the needle 1.

The control unit 8 can also displace the needle 1 by suitable motor means (not shown).

In the position in FIG. 1, the needle 1 is in the vicinity of an injection nozzle 10, which can convey a flow F of a reagent R in the direction of the open lower end 2 of the needle, in order to permit thorough mixing of an aliquot of blood A (ejected by the needle 1), and of the flow F of the reagent R.

The nozzle 10 is connected by means of a duct 11 to a second-volumetric distributor 12, comprising a syringe 13 activated by a step motor 14, which is also controlled by the control unit 8.

The injection nozzle 10 is supported by a mixing and/or measuring receptacle, in this case consisting of a vessel 15, which can receive the mixture formed from the aliquot of blood A and the flow F of reagent R.

Figure 2:
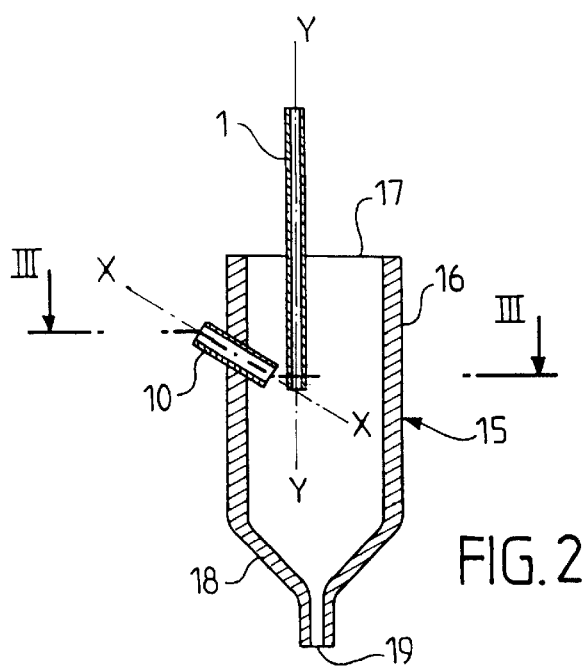
FIG. 2 is a detail of FIG. 1, showing the vessel, the needle and the injection nozzle.
Figure 3:
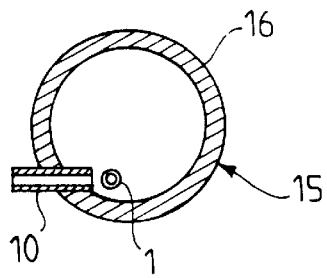
FIG. 3 is a view in transverse cross-section along line III—III in FIG. 2.

As can be seen more particularly in FIGS. 2 and 3, the vessel 15 is delimited mainly by a peripheral wall 16, which has a generally cylindrical shape and a vertical axis. This wall 16 has an open upper part 17, and is extended in its lower part by a frusto-conical wall 18, which leads to an outlet duct 19 for discharge of the mixture M.

The injection nozzle 10 has an axis XX (FIG. 2) which is slightly inclined relative to the horizontal, and intersects the axis YY of the needle 1. The latter is disposed in the vicinity of the wall 16 of the vessel 15, such that the aliquot of blood A is forced by the flow F of reagent to a point close to the wall 16, thus assisting thorough mixing of the blood and the reagent by means of a rotary motion which creates a type of eddy. The mixture M thus created is then measured and/or ejected through the outlet duct 19 of the vessel 15.

Figure 4:
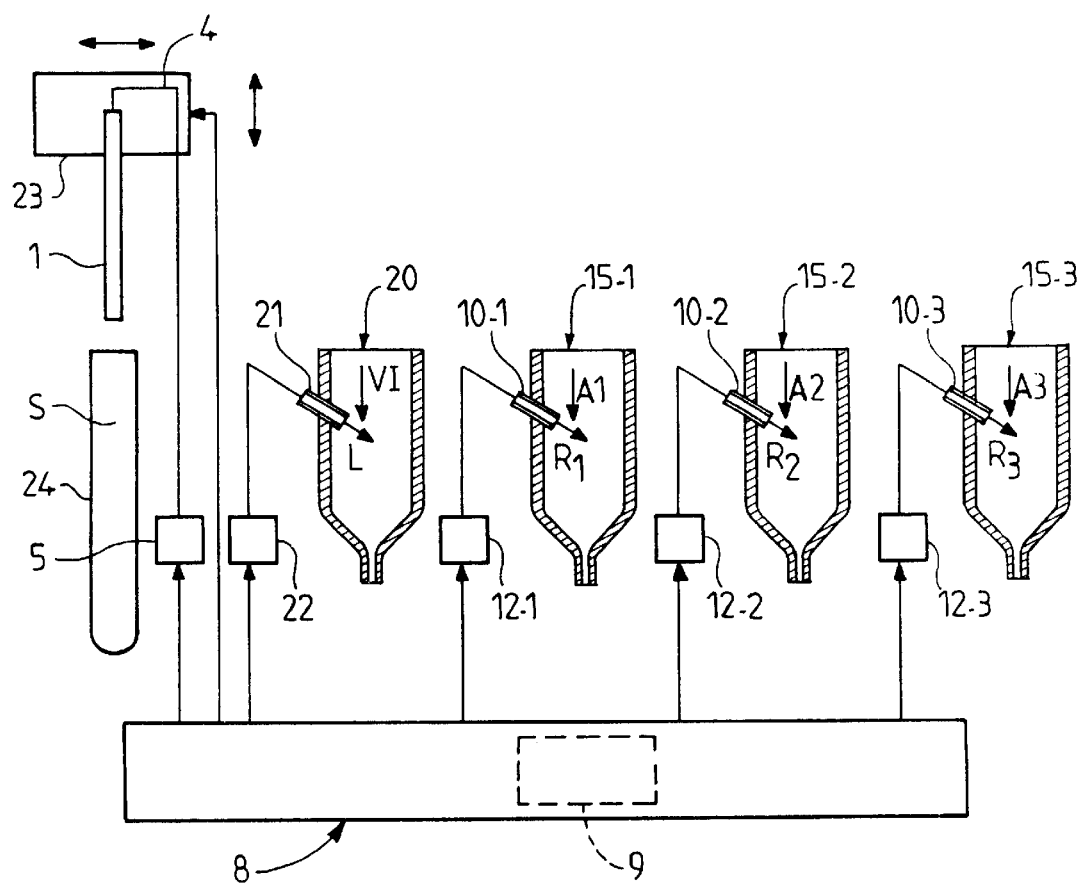
FIG. 4 is a schematic representation of a device according to the invention, comprising a rinsing vessel and three mixing and/or measuring vessels.

FIG. 4 shows schematically a device which is similar to that in FIG. 1, and comprises three mixing and/or analysis vessels 15-1, 15-2 and 15-3, which are similar to the vessel 15 previously described, and support respectively three injection nozzles 10-1, 10-2 and 10-3, which are similar to the injection nozzle 10 previously described.

These injection nozzles are connected respectively to three volumetric distributors 12-1, 12-2 and 12-3 (shown schematically), which are similar to the volumetric distributor 12 previously described.

On each occasion, the distributors 12-1, 12-2 and 12-3 can convey a specific volume of reagent into the corresponding vessel. The volumetric distributors 12-1. 12-2 and 12-3 are piloted by the control unit 8.

In the embodiment in FIG. 4, the device additionally comprises a rinsing vessel 20, with which there is associated an injection nozzle 21, which is connected to a volumetric distributor 22, in order to permit distribution of a rinsing fluid. The volumetric distributor 22 is also piloted by the control unit 8.

The latter also pilots motor means 23, which can displace the needle 1, and bring it in succession towards the rinsing vessel 20 and the vessels 15-1, 15-2 and 15-3, according to a sequence of operations programmed by the microprocessor 9.

Thus, the needle 1 can be introduced into an analysis tube 24 which contains the blood S of a patient, this tube being in the form of an open tube in the present case.

The motor means 23 can displace the needle in vertical or horizontal translation, as shown by the double arrows.

The functioning of the device in FIG. 4 is now described, by way of example.

The needle 1 is displaced by the motor means 23, under the control of the control unit 8, such as to penetrate in the interior of the analysis tube 24. The volumetric distributor 5 is then actuated by the control unit 8, in order to draw up a specific volume of blood, which constitutes a sample E. This sample E is contained in the needle 1, and is separated from the fluid L by an air bubble A (FIG. 5) which forms an interface, and thus prevents mixing between the blood and the fluid. The latter acts as an intermediary in order to control the drawing up into the needle 1, and ejection from it.

Figure 5:
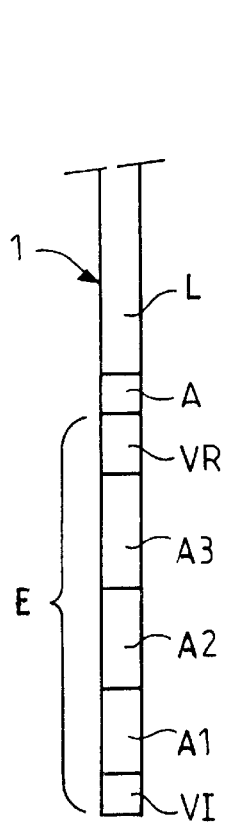
FIG. 5 shows schematically the content of a needle containing a blood sample, before the latter is distributed and fractionated.

The needle is then withdrawn from the tube 24, and subsequently moved such that it is positioned opposite the rinsing vessel 20, and is inserted in the latter. The volumetric distributor 5 is activated by the control unit 8, in order to eject an initial volume VI (see FIG. 5). This initial volume is received in the rinsing vessel, and is discharged by means of a flow of rinsing fluid L conveyed by the nozzle 21, under the action of the volumetric distributor 22 which is piloted by the control unit 8. The needle 1 is then extracted from the rinsing vessel 20, moved opposite the mixing and/or analysis vessel 15-1, and inserted in the latter, such that the end of the needle is positioned opposite the injection nozzle 10-1. The volumetric distributor 12-1 is then actuated by the control unit 8, in order to eject a fraction of the sample E, which corresponds to a first aliquot A1 (FIG. 5). This aliquot A1 is mixed with a flow of a first reagent R1 in order to produce a mixture, which is measured and/or collected at the outlet of the vessel 15-1.

The needle 1 is then extracted from the vessel 15-1, and is subsequently brought towards the vessels 15-2, 15-3, into which the aliquots A2 and A3 respectively (FIG. 5) are ejected. These aliquots are mixed with flows of reagent R2 and R3, in order to produce mixtures which are measured and/or collected at the outlet of the vessels 15-2 and 15-3.

After these operations, there remains in the needle a residual volume VR of blood (FIG. 5), which is still separated from the fluid L by the air bubble A. This residual volume VR must be discharged.

For this purpose, the needle 1 is displaced once more towards the rinsing vessel 20, and the residual volume VR is discharged by a flow of the rinsing fluid, which at the same time ensures that the lower end 2 of the needle 1 is cleaned, so that similar operations can be carried out on another sample.

The control unit 8 makes it possible to pilot the sequence of operations, such that drawing up of the blood sample, then distribution of the sample in aliquots obtained from fractionating of the sample, are carried out under very accurate controlled conditions.

The various volumetric distributors are each actuated by step motors, which consequently make it possible to collect by drawing up, or to distribute by ejection, very accurate volumes of blood, reagent or rinsing fluid, with flow rates which are likewise accurate.

In order to ensure that an aliquot of blood and a flow of reagent are mixed thoroughly in a mixing vessel, it is advantageous to carry out firstly injection of only an initial part of the flow of reagent, then simultaneous injection of the aliquot of blood and of an intermediate part of the flow of reagent, and to end by injection of only a final part of the flow of reagent.

By way of example, the initial, intermediate and final parts of the reagent can correspond respectively to approximately 10%, 80% and 10% of the total volume of the flow of reagent.

It will be appreciated that the above-described operating sequences can be subjected to many variants.

In particular, two successive mixing operations can be carried out in a single vessel, and a rinsing operation can be interposed between two mixing operations which involve different reagents etc.

In general, the mixing operations are carried out starting with the least pollutant or contaminating reagent, and ending with the most pollutant or contaminating reagent.

Figure 6:
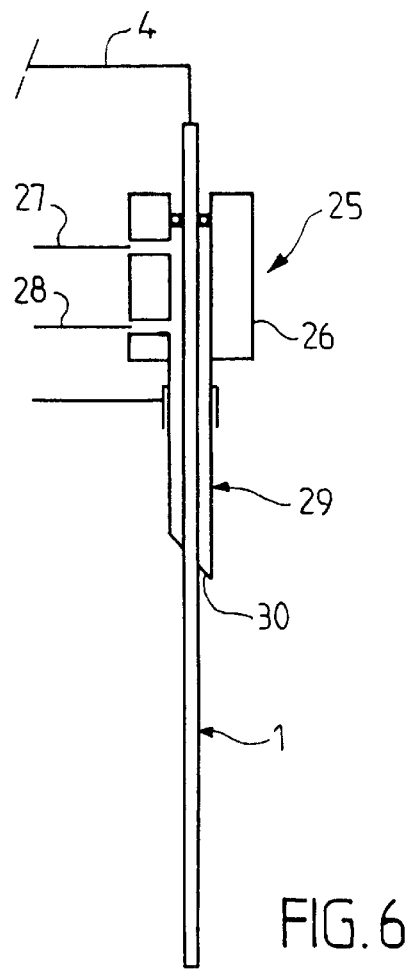
FIG. 6 is a schematic representation of a needle associated with a known cleaning device according to publication FR 2 707 760.

In the case in FIG. 6, the needle 1 is associated with a cleaning device 25 of the type described in publication FR 2 707 760 in the name of the applicant. This cleaning device substantially comprises a guiding unit 26, which contains an emptying duct 27 and a rinsing duct 28. In addition, the device 25 comprises a pre-piercing needle 29, which has a bevelled end 30 which can pierce the stopper (not shown) of an analysis tube.

Figure 7:
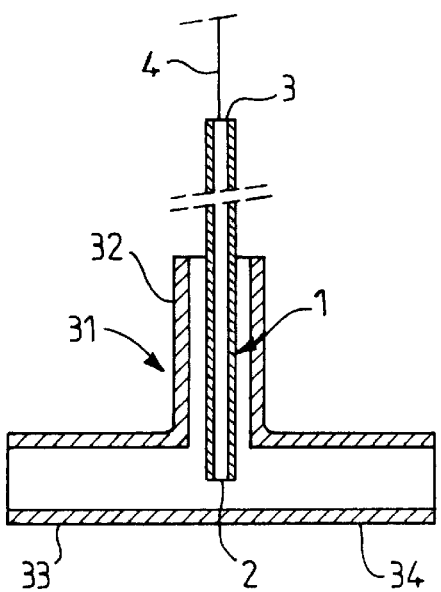
FIG. 7 is a view in longitudinal cross-section of a receptacle in the form of a T-shaped connection, this connection accommodating a sampling needle and an injection nozzle.

In the embodiment in FIG. 7, to which reference is now made, the mixing and/or measuring receptacle no longer consists of a vessel, but of a T-shaped connection 31, which has a first, vertical branch 32 in which the needle 1 can be introduced, a second, horizontal branch 33, in which the reagent is injected, and a third branch 34, which is opposite the branch 33, and acts as an outlet for the mixture. The branch 33 is disposed such that the flow of reagent reaches the open end 2 of the needle.

It will be appreciated that the invention is not limited to the embodiments previously described, and can be subjected to many variants.

The method and the device according to the invention provide considerable flexibility of use, particularly concerning the number and volume of the aliquots of blood to be processed.

What is claimed is:

1. A method for fractionated distribution of a blood sample, comprising the steps of:
   a) drawing up a blood sample into a needle;
   b) distributing via the needle an aliquot corresponding to a specific fraction of the blood sample drawn up, into a flow of a reagent, to thereby produce a mixture of the aliquot and the reagent;

c) collecting the mixture in a mixing and/or measuring receptacle; and d) repeating steps b) and c) at least once to distribute a further aliquot corresponding to a further specific fraction of the blood sample, into a further flow of reagent, wherein each of said aliquots has a predetermined volume, the volumes of said aliquots being identical or different.

2. The method of claim 1, wherein step a) comprises drawing the blood sample up into the needle, which already contains a fluid, and wherein a gas bubble is formed at an interface between the fluid and the blood sample.

3. The method of claim 1, wherein the blood sample is drawn up into the needle via a tube of an open or closed type, which contains a volume of blood to be analyzed.

4. The method of claim 1, wherein the fractions of the blood sample which are distributed have a total volume which is less than the blood sample which is drawn up into the needle.

5. The method of claim 1, wherein step b) comprises injection of the aliquot of blood, and injection of the flow of reagent under controlled conditions, and in a substantially simultaneous manner.

6. The method of claim 5, wherein step b) comprises in succession:

b1) injecting an initial part only of the flow of reagent;

b2) simultaneously injecting the aliquot of blood and of a major part of the flow of reagent; and b3) injecting a final part only of the flow of reagent.

7. The method of claim 5, wherein, in step b), the flow of reagent is injected such that this flow reaches the end of the needle via which the aliquot of blood is injected.

8. The method of claim 5, wherein the aliquot of blood is injected in a substantially vertical descending direction, and the flow of reagent is injected in a direction which is horizontal or inclined relative to the horizontal.

9. The method of claim 1, additionally comprising depositing an aliquot of blood in a fluid medium or on a solid support.

* * * * *